US008603738B2

(12) United States Patent
Condeelis et al.

(10) Patent No.: US 8,603,738 B2

(45) Date of Patent: Dec. 10, 2013

(54) METASTASIS SPECIFIC SPLICE VARIANTS OF MENA AND USES THEREOF IN DIAGNOSIS, PROGNOSIS AND TREATMENT OF TUMORS

(75) Inventors: John S. Condeelis, Bronx, NY (US); Sumanta Goswami, Larchmont, NY (US); Frank Gertler, Boston, NY (US); Paola Nisticò, Rome (IT)

(73) Assignees: Albert Einstein College of Medicine of Yeshiva University, Bronx, NY (US); Massachusetts Institute of Technology, Cambridge, MA (US); IFO-Regina Elena Cancer Institute, Rome (IT)

( * ) Notice: Subject to any disclaimer, the term of this patent is extended or adjusted under 35 U.S.C. 154(b) by 728 days.

(21) Appl. No.: 12/462,324

(22) Filed: Jul. 31, 2009

(65) Prior Publication Data

US 2010/0047240 A1 Feb. 25, 2010

Related U.S. Application Data

(63) Continuation-in-part of application No. PCT/US2008/001343, filed on Jan. 31, 2008.

(60) Provisional application No. 60/899,303, filed on Feb. 2, 2007.

(51) Int. Cl.

| | |
|---|---|
| ***C12Q 1/68*** | (2006.01) |
| ***G01N 33/53*** | (2006.01) |
| ***G01N 33/577*** | (2006.01) |
| ***G01N 33/68*** | (2006.01) |
| *C07K 14/435* | (2006.01) |

(52) U.S. Cl.

USPC .......... 435/6.1; 435/7.1

(58) Field of Classification Search

USPC .......... 435/6.1, 7.1

See application file for complete search history.

(56) References Cited

U.S. PATENT DOCUMENTS

| | | | |
|---|---|---|---|
| 5,912,128 | A | 6/1999 | Lal et al. |
| 5,990,087 | A | 11/1999 | Lal et al. |
| 6,645,499 | B1 | 11/2003 | Lal et al. |
| 6,716,597 | B2 | 4/2004 | Gertler et al. |
| 2006/0040262 | A1 | 2/2006 | Morris et al. |
| 2008/0138805 | A1 | 6/2008 | Condeelis |
| 2011/0059470 | A1 | 3/2011 | Condeelis et al. |
| 2011/0296538 | A1 | 12/2011 | Segall et al. |

FOREIGN PATENT DOCUMENTS

| | | | |
|---|---|---|---|
| WO | WO 98/01755 | | 1/1998 |
| WO | WO/2004/060304 | A2 | 7/2004 |
| WO | WO 2006/017635 | A2 | 2/2006 |
| WO | WO 2008/097466 | A2 | 8/2008 |

OTHER PUBLICATIONS

Di Modugno, F., et al. Clin. Cancer Res. 12(5): 1470-21478, 2006.*
Di Modugno F et al., Human Mena protein, a serex-defined antigen overexpressed in breast cancer eliciting both humoral and CD8+ T-cell immune response, Int J. Cancer 109(6):909-18, 2004.
Di Modugno F et al., Molecular Cloning of hMena (ENAH) and Its Splice Variant hMena +11a: Epidermal Growth Factor Increases Their Expression and Stimulates hMena+11a phosphorylation in Breast Cancer Cell Lines, Cancer Res 67: 2657-2665, 2007.
Gertler F, Mena, a relative of VASP and Drosophila Enabled, is implicated in the control of microfilament dynamics, Cell 87(2):227-39, 1996, Abstract Only.
Goswami S et al., Identification of invasion specific splice variants of the cytoskeletal protein Mena present in mammary tumor cells during invasion in vivo, Clin Exp Metastasis, 2009, 26:153-159; published online Nov. 5, 2008.
Philippar U et al., A Mena Invasion Isoform Potentiates EGF-Induced Carcinoma Cell Invasion and Metastasis, Developmental Cell 15: 813-828, Dec. 9, 2008.
Pino M et al., Human Mena+11a isoform serves as a marker of epithelial phenotype and sensitivity to epidermal growth factor receptor inhibition in human pancreatic cancer cell lines, Clin Cancer Res., Aug. 1, 2008;14(15):4943-50, Abstract Only.
Robinson B et al., Tumor Microenvironment of Metastasis in Human Breast Carcinoma: A Potential Prognostic Marker Linked to Hematogenous Dissemination, Clin Cancer Res 2009;15(7) Apr. 1, 2009, 2433-2441.
Toyoda A et al., Aberrant expression of human ortholog of mammalian enabled (hMena) in human colorectal carcinomas: implications for its role in tumor progession, Int J. Oncol Jan. 2009;34(1):53-60, Abstract Only.
Wang W et al. Identification and Testing of a Gene Expression Signature of Invasive Carcinoma Cells within Primary Mammary Tumors, Cancer Research 64: 8585-8594, 2004.
Wang W et al. Single Cell Behavior in Metastatic Primary Mammary Tumors Correlated with Gene Expression Patterns Revealed by Molecular Profiling, Cancer Research 62: 6278-6288 Nov. 1, 2002.
Wang W et al., Gene expression analysis on small number of invasive cells collectted by chemotaxis from primary mammary tumors of the mouse, BMC Biotechnology 3:13, 2003 http://www.biomedcentral.com/1472-6750/3/13, 12 pages.
PCT Notification of Transmittal of the Int'l Search Report and The Written Opinion of the Int'l Searching Authority dated Sep. 11, 2008 in connection with PCT/US2008/01343, 12 pgs.
Gurzu S et al., The immunohistochemical aspects of protein Mena in cervical lesions, Rom J Morphol Embryol, 2009;50(2):213-6, Abstract Only.
Gurzu S et al., The expression of cytoskeleton regulatory protein Mena in colorectal lesions, Rom J Morphol Embryol, 2008;49(3):345-9, Abstract Only.
PCT Notification Concerning Transmittal of International Preliminary Report on Patentability dated Aug. 13, 2009 in connection with PCT International Patent Application No. PCT/US2008/001343, 2 pages.
PCT Written Opinion of the International Searching Authority dated Sep. 11, 2008 in connection with PCT International Patent Application No. PCT/US2008/001343, 4 pages.

(Continued)

*Primary Examiner* — Misook Yu
*Assistant Examiner* — Anne Holleran
(74) *Attorney, Agent, or Firm* — Amster, Rothstein & Ebenstein LLP

(57) ABSTRACT

Methods and kits for diagnosis, prognosis and treatment of metastatic tumors are provided where the metastatic tumor is characterized by changes in expression of +++, ++ and/or 11a variants of Mena.

34 Claims, 12 Drawing Sheets

(56) References Cited

OTHER PUBLICATIONS

Communication Supplementary European Search Report dated May 7, 2010 received from the European Patent Office in connection with European Patent Application No. 08713370.0, 4 pages.

Di Modugno F et al., entitled "hMean+11a is an epithelial-restricted hMena isoform which is phosphorylated along the pathway of ErbB tyrosine kinase receptors," 98th AACR Annual Meeting, Apr. 14-18, 2007, Los Angeles, CA, Abstract Only, 2 pages.

Roussos E T et al., entitled "Mena deficiency delays tumor progression and decreases metastasis in polyoma middle-T transgenic mouse mammary tumors," Breast Cancer Reserach, 2010, 12:R101, pp. 1-16.

Gertler F B et al., entitled "Mena, a Relative of VASP and Drosophila Enabled, Is Implicated in the Control of Microfilament Dynamics," Cell, vol. 87, Oct. 18, 1996, pp. 227-239.

* cited by examiner

MDA 231 T47D

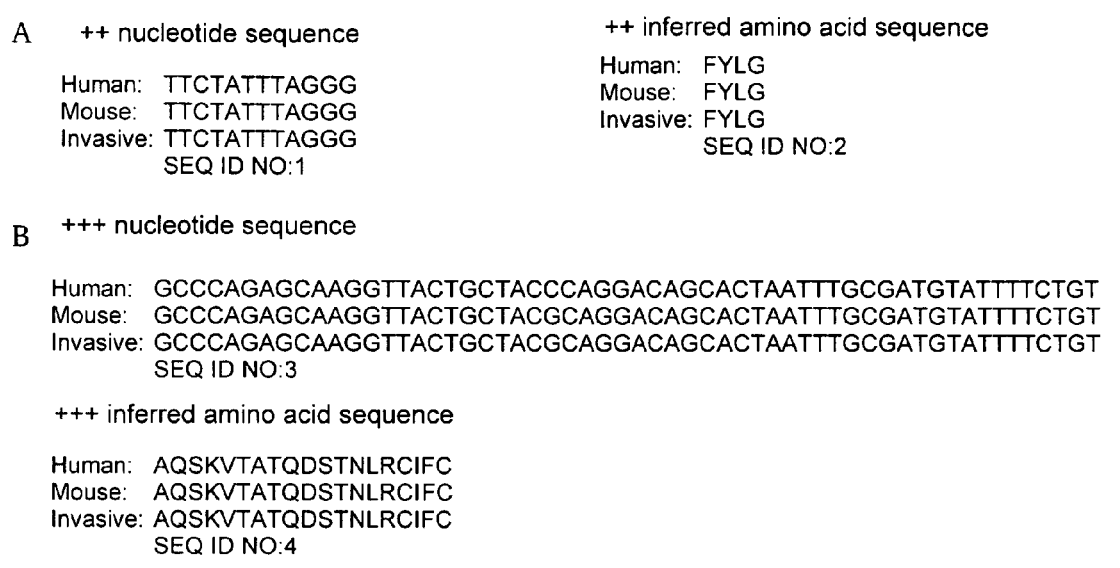

A ++ nucleotide sequence

Human: TTCTATTTAGGG
Mouse: TTCTATTTAGGG
Invasive: TTCTATTTAGGG
SEQ ID NO:1

++ inferred amino acid sequence

Human: FYLG
Mouse: FYLG
Invasive: FYLG
SEQ ID NO:2

B +++ nucleotide sequence

Human: GCCCAGAGCAAGGTTACTGCTACCCAGGACAGCACTAATTTGCGATGTATTTTCTGT
Mouse: GCCCAGAGCAAGGTTACTGCTACGCAGGACAGCACTAATTTGCGATGTATTTTCTGT
Invasive: GCCCAGAGCAAGGTTACTGCTACGCAGGACAGCACTAATTTGCGATGTATTTTCTGT
SEQ ID NO:3

+++ inferred amino acid sequence

Human: AQSKVTATQDSTNLRCIFC
Mouse: AQSKVTATQDSTNLRCIFC
Invasive: AQSKVTATQDSTNLRCIFC
SEQ ID NO:4

FIGURE 4A-4B

Expression of Mena Splice Variants in FNA Samples form Human Breast Lesions

| | 4109 FA | 5609 IDC | 41609 IDC | 42409 IDC | 52009 IDC |
|---|---|---|---|---|---|
| Mena +++ | 1 | 0.3 | 3.39 | 37.84 | 10.99 |
| Mena 11a | 1 | 0.04 | 0 | 0 | 0.17 |

METASTASIS SPECIFIC SPLICE VARIANTS OF MENA AND USES THEREOF IN DIAGNOSIS, PROGNOSIS AND TREATMENT OF TUMORS

CROSS-REFERENCE TO RELATED APPLICATION

This application is a continuation-in-part of and claims priority of PCT International Patent Application No. PCT/US2008/001343, filed Jan. 31, 2008, which designates the United States of America and which claims the benefit of U.S. Provisional Patent Application No. 60/899,303, filed Feb. 2, 2007, the contents of which are incorporated by reference.

STATEMENT OF GOVERNMENT SUPPORT

This invention was made with government support under grant number CA100324 awarded by the National Cancer Institute, U.S. Department of Health and Human Services. The government has certain rights in the invention.

BACKGROUND OF THE INVENTION

Various publications are referred to in parentheses throughout this application. Full citations for these references may be found at the end of the specification immediately preceding the claims. The disclosures of these publications are hereby incorporated by reference in their entireties into the subject application to more fully describe the art to which the subject application pertains.

One out of three cancers diagnosed among U.S. women is due to breast cancer; 212,920 new invasive breast cancer cases and an additional 61,980 in situ breast cancer cases are expected to be diagnosed in the U.S. in 2006. Around 40,970 women are expected to die from breast cancer in 2006 in the U.S. alone (American Cancer Society, Breast Cancer Facts and Figures 2006). The metastasis of 10-15% of patients with breast cancer is aggressive and can take between 3-10 years to be manifested after the initial diagnosis. Currently, the prognosis in 70% of patients cannot be accurately determined resulting in the unnecessary treatment of many patients who will not benefit and may be injured by radiation and chemotherapy. The availability of an antibody and associated polymerase chain reaction (PCR) primer pair that uniquely and specifically identifies metastatic disease will allow for accurate prediction of disease course and allow appropriate treatment.

Invasion of tumor cells into surrounding tissue and intravasation into blood and lymphatic vessels is implicated in the progression of metastatic breast cancer. This multi-step process involves a number of phenotypic changes which occur sequentially and give rise to a hyper-invasive cell (Condeelis et al., 2005). In an effort to identify these individual events and to understand the molecular events underlying these phenotypic changes, animal models have been developed as well as a chemotaxis assay that isolates the in vivo invasive cells from the average primary tumor cells (APTC) (Wyckoff et al., 2000). Chemotaxis based isolation of the invasive cells and subsequent gene expression analysis have resulted in the identification of an invasion specific gene expression signature in invasive cells (Wang et al., 2004). In these studies a number of genes have been identified which need to be coordinately up-regulated in the invasive cells in order for invasion to lead to metastasis (Wang et al., 2006).

One of the key genes of the invasion signature is that coding for the cytoskeletal protein Mena. Mena is a member of the Ena/VASP family of proteins. These proteins are regulatory molecules which control cell movement, motility and shape in a number of cell types and organisms. They are proposed to function by preventing the actin filaments from being capped by capping proteins at their barbed ends (Barzik et al., 2005). The anti-capping activity of Mena has been proposed to amplify the barbed end output of the cofilin and Arp2/3 complex pathways, which is sufficient to increase metastatic potential in mammary tumors (Wang et al., 2006). Ena/VASP proteins are also constituents of the adherence junctions necessary to seal membranes in the epithelial sheet and control actin organization on cadherin adhesion contact (Scott et al., 2006). This process is frequently perturbed in cancer. Ena/VASP proteins contain specific domains including the N-terminal EVH1 domain, which plays an essential role in intracellular protein localization by interacting with proline-rich motifs found in proteins such like zyxin and vinculin (Prehoda et al., 1999). The proline-rich domain in the center is known to mediate interaction with proteins having the SH3 and WW domains and also with the actin monomer binding protein profilin (Gertler et al., 1996). The C-terminal domain of Mena contains an EVH2 domain that is involved in tetramerization of the protein and also binding to G- and F-actin (Kuhnel et al., 2004). The interaction of the EVH2 domain with the growing ends of the actin filaments is essential for targeting the Ena/VASP to lamellipodia and filopodia (Loureiro et al., 2002). Mena is upregulated in mouse and rat invasive breast cancer cells (Wang et al., 2004) and overexpressed in human breast cancer tissues (Di Modugno et al., 2004). Both mouse and human Mena homologs have been cloned and sequenced, and a number of splice variants have been identified (Gertler et al., 1996; Urbanelli et al., 2006).

Recently it has been shown that splice variants can work very efficiently as cancer biomarkers (Brinkman 2004; Venables 2006). However, there remains a need to identify splice variants that are upregulated specifically in metastatic cancer cells, such as metastatic breast cancer cells.

SUMMARY OF THE INVENTION

The invention provides a method for determining whether a subject has a metastatic tumor comprising assaying a blood, tissue and/or tumor sample of the subject for expression of the ++ and/or +++ variant of Mena, wherein overexpression of the ++ and/or +++ variant of Mena indicates the presence of a metastatic tumor.

The invention also provides a method for determining whether a subject has a metastatic tumor comprising assaying a blood, tissue and/or tumor sample of the subject for expression of the ++ and/or +++, and 11a variants of Mena, wherein overexpression of the ++ and/or +++ variants and decreased expression of the 11a variant of Mena, together, indicates the presence of a metastatic tumor.

The invention provides a method for assessing the efficacy of therapy to treat a metastatic tumor in a subject who has undergone or is undergoing treatment for a metastatic tumor, the method comprising assaying a blood, tissue and/or tumor sample of the subject for expression of the ++ and/or +++ variant of Mena, wherein overexpression of the ++ and/or +++ variant of Mena is indicative of a need to continue therapy to treat the tumor.

The invention also provides a method for assessing the efficacy of therapy to treat a metastatic tumor in a subject who has undergone or is undergoing treatment for a metastatic tumor, the method comprising assaying a blood, tissue and/or tumor sample of the subject for expression of the ++ and/or +++, and 11a variants of Mena, wherein overexpression of the ++ and/or +++ variants and decrease in expression of 11a variant of Mena is indicative of a need to continue therapy to treat the tumor.

The invention further provides a method for assessing the prognosis of a subject who has a metastatic tumor, comprising assaying a blood, tissue and/or tumor sample of the subject for expression of the ++ and/or +++ variant of Mena, wherein the subject's prognosis improves with a decrease in expression of the ++ and/or +++ variant of Mena.

The invention further also provides a method for assessing the prognosis of a subject who has a metastatic tumor, comprising assaying a blood, tissue and/or tumor sample of the subject for expression of the ++ and/or +++, and 11a variants of Mena, wherein the subject's prognosis improves with a decrease in expression of the ++ and/or +++ variants of Mena, and an increase in the 11a variant of Mena.

The invention provides a method of inhibiting metastasis of a tumor in a subject, the method comprising reducing the presence or activity of the ++ isoform (SEQ ID NO:2) and/or +++ isoform (SEQ ID NO:4) of Mena in the subject and/or increasing the presence or activity of Mena 11a (SEQ ID NO:24).

The invention provides a method for screening for a candidate compound that inhibits metastasis of a tumor, the method comprising contacting the compound with a cell line or tissue culture that express the ++ isoform (SEQ ID NO:2) and/or +++ isoform (SEQ ID NO:4) of Mena and/or Mena 11a (SEQ ID NO:24), wherein reduction in the expression of the ++ and/or +++ isoform of Mena is indicative that the compound is a candidate compound for inhibiting metastasis of a tumor or wherein lack of reduction in the expression of the ++ and/or +++ isoform of Mena is indicative that the compound is not a candidate compound for inhibiting metastasis of a tumor, and/or wherein increase in the expression of Mena 11a is indicative that the compound is a candidate compound for inhibiting metastasis of a tumor or wherein lack of increase in the expression of Mena 11a is indicative that the compound is not a candidate compound for inhibiting metastasis of a tumor.

The invention provides a purified polypeptide, where the polypeptide is overexpressed in a metastatic tumor, and an isolated nucleic acid molecule encoding the polypeptide, where the polypeptide comprises the amino acid sequence of the ++ isoform (SEQ ID NO:2) and/or +++ isoform (SEQ ID NO:4) of Mena.

The invention provides kits for detecting the presence or absence of a metastatic tumor, where the kits comprise an antibody, a peptide or an aptamer that specifically binds to the ++ isoform (SEQ ID NO:2) or +++ isoform (SEQ ID NO:4) of Mena or Mena 11a (SEQ ID NO:24) and/or a probe or PCR primers that specifically hybridize to nucleic acid encoding the ++ isoform (SEQ ID NO:2) or +++ isoform (SEQ ID NO:4) of Mena or Mena 11a (SEQ ID NO:24).

BRIEF DESCRIPTION OF THE DRAWINGS

FIG. 4A-4B. Sequence alignment for ++ and +++ exons in invasive cells aligned with published mouse and human sequences. The ++ exon nucleotides (SEQ ID NO:1) and their inferred amino acid sequence (SEQ ID NO:2) are aligned in A and the +++ exon nucleotides (SEQ ID NO:3) and their inferred amino acid sequence (SEQ ID NO:4) are aligned in B.

DETAILED DESCRIPTION OF THE INVENTION

Figure 1A:
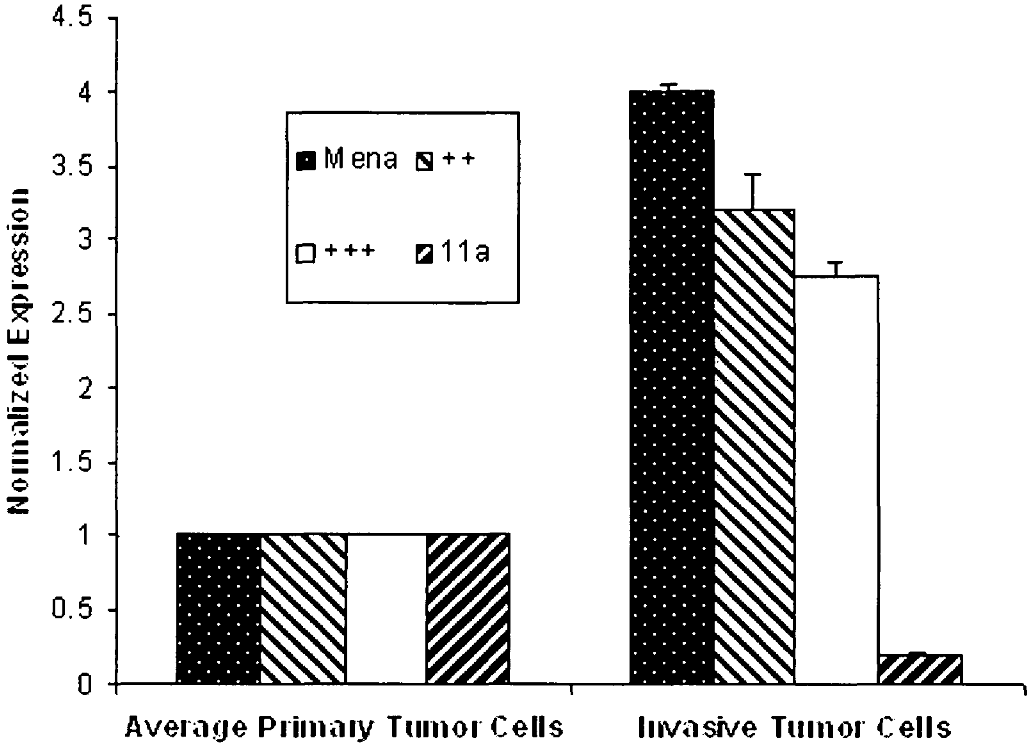
FIG. 1A-1B. Quantification of Mena isoforms by QRT-PCR in MTLn3 rat allograft model (A) and PyMT mouse transgenic model (B). The expression of transcripts containing Mena++ and Mena+++ exons are upregulated while those containing Mena 11a are downregulated specifically in the invasive tumor cell population as compared to the APTC. The levels of transcript observed using pan Mena primers (Mena), and ++ and +++ primers are increased while that observed using 11a primers is greatly reduced in both animal tumor models. *11a message was undetectable in the PyMT mouse transgenic invasive tumor cells. The error bars show standard errors of mean (SEM) performed on three biological repeats and three technical repeats.

The invention provides a method for determining whether a subject has a metastatic tumor comprising assaying a blood, tissue and/or tumor sample of the subject for expression of the ++ and/or +++ variant of Mena, wherein overexpression of the ++ and/or +++ variant of Mena indicates the presence of a metastatic tumor.

The invention also provides a method for assessing the efficacy of therapy to treat a metastatic tumor in a subject who has undergone or is undergoing treatment for a metastatic tumor, the method comprising assaying a blood, tissue and/or tumor sample of the subject for expression of the ++ and/or +++ variant of Mena, wherein overexpression of the ++ and/or +++ variant of Mena is indicative of a need to continue therapy to treat the tumor.

The invention further provides a method for assessing the prognosis of a subject who has a metastatic tumor, comprising assaying a blood, tissue and/or tumor sample of the subject for expression of the ++ and/or +++ variant of Mena, wherein the subject's prognosis improves with a decrease in expression of the ++ and/or +++ variant of Mena.

In any of the methods, the expression of the ++ and/or +++ variant of Mena can be compared to expression of Mena 11a, i.e. Mena++/Mena11a expression ratio or Mena+++/Mena 11a expression ratio.

The method for determining whether a subject has a metastatic tumor can comprise assaying a blood, tissue and/or tumor sample of the subject for expression of the ++ and/or +++, and 11a variants of Mena, wherein overexpression of the ++ and/or +++ variants and decreased expression of the 11a variant of Mena, together, indicate the presence of a metastatic tumor. The method for assessing the efficacy of therapy to treat a metastatic tumor in a subject can comprise assaying a blood, tissue and/or tumor sample of the subject for expression of the ++ and/or +++, and 11a variants of Mena, wherein overexpression of the ++ and/or +++ variants and decreased expression of the 11a variant of Mena is indicative of a need to continue therapy to treat the tumor. The method for assessing the prognosis of a subject who has a metastatic tumor can comprise assaying a blood, tissue and/or tumor sample of the subject for expression of the ++ and/or +++, and 11a variants of Mena, wherein the subject's prognosis improves with a decrease in expression of the ++ and/or +++ variants of Mena and an increase in expression of the 11a variant of Mena.

The tumor can be, for example, a secretory epithelial tumor. The tumor can be, for example, a breast, pancreas, prostate, colon, brain, liver, lung, head or neck tumor.

As used herein, changes in the expression of the ++, +++ and 11a variants of Mena mean changes in expression relative to their levels in normal tissue or relative to their levels in in situ (non-metastatic) carcinomas. The expression of the ++, +++ or 11a Mena variant can be normalized relative to the expression of protein variants that are not changed in expression in a metastatic tumor. Examples of proteins that could be used as controls include those of the Ena/VASP family that are unchanged in their expression in metastatic cells, including the 140K and 80K isoforms of Mena, and VASP. Other examples of proteins or genes that could be used as controls include those listed as relatively unchanged in expression in Condeelis et al. (2005). Such controls include N-WASP, Rac1, Pak1, and PKCalpha and beta. Preferred controls include the 80K and 140K isoforms of Mena and VASP.

The expression of the ++, +++ and/or 11a variants of Mena may be detected in vitro or in vivo. The expression may be detected at the level of the nucleic acid variant and/or at the level of the protein isoform. Where expression is detected in vitro, a sample of blood, tumor, tissue or cells from the subject may be removed using standard procedures, including biopsy and aspiration. Cells which are removed from the subject may be analyzed using immunocytofluorometry (FACS analysis). The expression of the ++, +++ and/or 11a variants of Mena may be detected by detection methods readily determined from the known art, including, without limitation, immunological techniques such as Western blotting, hybridization analysis, fluorescence imaging techniques, and/or radiation detection.

The blood, tissue, cell or tumor sample can be assayed using an agent that specifically binds to the ++ isoform (SEQ ID NO:2) or +++ isoform (SEQ ID NO:4) or 11a (SEQ ID NO:24) (Table 1) of Mena. The agent that specifically binds to Mena ++, +++ or 11a can be, for example, an antibody, a peptide or an aptamer. As used herein, the term "antibody" encompasses whole antibodies and fragments of whole antibodies wherein the fragments specifically bind to Mena ++, +++ or 11a. Antibody fragments include, but are not limited to, $F(ab')_2$ and Fab' fragments and single chain antibodies. $F(ab')_2$ is an antigen binding fragment of an antibody molecule with deleted crystallizable fragment (Fc) region and preserved binding region. Fab' is ½ of the $F(ab')_2$ molecule possessing only ½ of the binding region. The term antibody is further meant to encompass polyclonal antibodies and monoclonal antibodies. Antibodies may be produced by techniques well known to those skilled in the art. Polyclonal antibody, for example, may be produced by immunizing a mouse, rabbit, or rat with purified polypeptides encoded by the ++ and/or +++ variants of Mena. Monoclonal antibody may then be produced by removing the spleen from the immunized mouse, and fusing the spleen cells with myeloma cells to form a hybridoma which, when grown in culture, will produce a monoclonal antibody. The antibody can be, e.g., any of an IgA, IgD, IgE, IgG, or IgM antibody. The IgA antibody can be, e.g., an IgA1 or an IgA2 antibody. The IgG antibody can be, e.g., an IgG1, IgG2, IgG2a, IgG2b, IgG3 or IgG4 antibody. A combination of any of these antibodies subtypes can also be used. One consideration in selecting the type of antibody to be used is the size of the antibody. For example, the size of IgG is smaller than that of IgM allowing for greater penetration of IgG into tissues. The antibody can be a human antibody or a non-human antibody such as a goat antibody or a mouse antibody. Antibodies can be "humanized" using standard recombinant DNA techniques.

TABLE 1

| Human Mena Sequences | |
|---|---|
| **Mena ++** | |
| FYLG | (SEQ ID NO: 2) |
| ttctatttag gg | (SEQ ID NO: 1) |
| **Mena +++** | |
| AQSKVTATQD STNLRCIFC | (SEQ ID NO: 4) |
| gcccagagca aggttactgc tacccaggac agcactaatt tgcgatgtat tttctgt | (SEQ ID NO: 3) |
| **Mena 11a** | |
| RDSPRKNQIV FDNRSYDSLH R | (SEQ ID NO: 24) |
| acgggattct ccaaggaaaa atcagattgt ttttgacaac aggtcctatg attcattaca cag | (SEQ ID NO: 25) |

Aptamers are single stranded oligonucleotides or oligonucleotide analogs that bind to a particular target molecule, such as a protein. Thus, aptamers are the oligonucleotide analogy to antibodies. However, aptamers are smaller than antibodies. Their binding is highly dependent on the secondary structure formed by the aptamer oligonucleotide. Both RNA and single stranded DNA (or analog) aptamers can be used. Aptamers that bind to virtually any particular target can be selected using an iterative process called SELEX, which stands for Systematic Evolution of Ligands by EXponential enrichment.

The agent that specifically binds to Mena ++, +++ or 11a may be labeled with a detectable marker. Labeling may be accomplished using one of a variety of labeling techniques, including peroxidase, chemiluminescent, and/or radioactive labels known in the art. The detectable marker may be, for example, a nonradioactive or fluorescent marker, such as biotin, fluorescein (FITC), acridine, cholesterol, or carboxy-X-rhodamine, which can be detected using fluorescence and other imaging techniques readily known in the art. Alternatively, the detectable marker may be a radioactive marker, including, for example, a radioisotope. The radioisotope may be any isotope that emits detectable radiation, such as, for example, $^{35}S$, $^{32}P$, or $^{3}H$. Radioactivity emitted by the radioisotope can be detected by techniques well known in the art. For example, gamma emission from the radioisotope may be detected using gamma imaging techniques, particularly scintigraphic imaging.

The expression of Mena ++, +++ or 11a in a subject may be detected through hybridization analysis of nucleic acid extracted from a blood, tumor, tissue or cell sample from the subject using one or more nucleic acid probes which specifically hybridize to nucleic acid encoding Mena ++, +++ or 11a. The nucleic acid encoding the ++ isoform of Mena can have the nucleotide sequence set forth in SEQ ID NO:1. The nucleic acid encoding the +++ isoform of Mena can have the nucleotide sequence set forth in SEQ ID NO:3. The nucleic acid encoding Mena 11a can have the nucleotide sequence set forth in SEQ ID NO:25. The nucleic acid probes may be DNA or RNA, and may vary in length from about 8 nucleotides to the entire length of the ++ or +++ nucleic acid variant of Mena. Hybridization techniques are well known in the art, see e.g. Sambrook and Russell (2001). The probes may be prepared by a variety of techniques known to those skilled in the art, including, without limitation, restriction enzyme digestion of Mena nucleic acid; and automated synthesis of oligonucleotides whose sequence corresponds to selected portions of the nucleotide sequence of the Mena nucleic acid, using commercially-available oligonucleotide synthesizers, such as the Applied Biosystems Model 392 DNA/RNA synthesizer. Combinations of two or more nucleic acid probes, corresponding to different or overlapping regions of nucleic acid encoding Mena ++, +++ or 11a may be used to assay a diagnostic sample for expression of Mena ++, +++ or 11a.

The nucleic acid probes may be labeled with one or more detectable markers. Labeling of the nucleic acid probes may be accomplished using a number of methods known in the art (e.g., nick translation, end labeling, fill-in end labeling, polynucleotide kinase exchange reaction, random priming, or SP6 polymerase) with a variety of labels (e.g., radioactive labels, such as $^{35}S$, $^{32}P$, or $^{3}H$, or nonradioactive labels, such as biotin, fluorescein (FITC), acridine, cholesterol, or carboxy-X-rhodamine (ROX)).

The sample can be assayed using PCR primers that specifically hybridize to nucleic acid encoding the ++ isoform (SEQ ID NO:2) or +++ isoform (SEQ ID NO:4) of Mena or Mena 11a (SEQ ID NO:24). The nucleic acid encoding the ++ isoform of Mena can have the nucleotide sequence set forth in SEQ ID NO:1. The nucleic acid encoding the +++ isoform of Mena can have the nucleotide sequence set forth in SEQ ID NO:3. The nucleic acid encoding Mena 11a can have the nucleotide sequence set forth in SEQ ID NO:25.

The sample can be assayed for the ++ variant of Mena, for the +++ variant of Mena, or for both the ++ variant and the +++ variant of Mena.

In addition, or alternatively, other splice variants of Mena may be overexpressed during metastasis of some tumors.

Overexpression of the ++ and/or +++ variant of Mena can occur in combination with overexpression of one or more of, for example, Arp 2/3 complex subunit p21, Arp 2/3 complex subunit p16, actinin alpha 3, capping protein alpha 1, epidermal growth factor receptor (EGFR), WAVE 3, actin gamma, LIM-kinase 1, cofilin 1, Rock 1, RhoA or protein kinase Cz. The detection of the expression of these genes has been described (e.g., Kamai et al., 2003; Otsubo et al., 2004; Wang et al., 2004).

The invention still further provides methods of inhibiting metastasis of a tumor in a subject, the method comprising reducing the presence or activity of the ++ isoform (SEQ ID NO:2) and/or +++ isoform (SEQ ID NO:4) of Mena in the subject. The method can also include increasing the presence or activity of Mena 11a (SEQ ID NO:24) in the subject. The method can involve intervention at the level of DNA, RNA, and/or protein. For example, the presence or activity of the isoform can be reduced by addition of an antisense molecule, a ribozyme, or an RNA interference (RNAi) molecule to the tumor, where the antisense molecule, ribozyme or RNAi molecule specifically inhibits expression of the isoform. The antisense molecule, ribozyme, or RNAi molecule can be comprised of nucleic acid (e.g., DNA or RNA) or nucleic acid mimetics (e.g., phosphorothionate mimetics) as are known in the art. Methods for treating tissue with these compositions are also known in the art. The antisense molecule, ribozyme or RNAi molecule can be added directly to the cancerous tissue in a pharmaceutical composition that preferably comprises an excipient that enhances penetration of the antisense molecule, ribozyme or RNAi molecule into the cells of the tissue. The antisense molecule, ribozyme or RNAi can be expressed from a vector that is transfected into the cancerous tissue. Such vectors are known in the art.

The presence or activity of the isoform can be reduced by addition of an antibody or aptamer to the tissue, wherein the antibody or aptamer specifically binds to and reduces the activity of the isoform in the tissue. The antibody or aptamer can be added directly to the tissue, preferably in a pharmaceutical composition comprising an agent that enhances penetration of the antibody or aptamer into the tissue. The antibody or aptamer can be encoded on a vector that is used to transfect the cancerous tissue.

The invention also provides methods for screening for a candidate compound that inhibits metastasis of a tumor, where the method comprises contacting the compound with a cell line or tissue culture that express the ++ isoform (SEQ ID NO:2) and/or +++ isoform (SEQ ID NO:4) of Mena and/or Mena 11a (SEQ ID NO:24), wherein reduction in the expression of the ++ and/or +++ isoform is indicative that the compound is a candidate compound for inhibiting metastasis of a tumor or wherein lack of reduction in the expression of the ++ and/or +++ isoform of Mena is indicative that the compound is not a candidate compound for inhibiting metastasis of a tumor, and/or wherein increase in the expression of Mena 11a is indicative that the compound is a candidate compound for inhibiting metastasis of a tumor or wherein lack of increase in the expression of Mena 11a is indicative that the compound is not a candidate compound for inhibiting metastasis of a tumor.

The invention provides a purified polypeptide, where the polypeptide is overexpressed in a metastatic tumor, the polypeptide comprising the amino acid sequence of the ++ isoform (SEQ ID NO:2) and/or +++ isoform (SEQ ID NO:4) of Mena. The invention also provides isolated nucleic acids encoding these polypeptides. The isolated nucleic acid can be DNA or RNA. The nucleic acid can comprise the nucleotide sequence for ++ variant (SEQ ID NO: 1) and/or +++ variant (SEQ ID NO:3) of Mena.

Laboratory tests of patient biopsy tissue using standard protocols for detection of the expression of nucleic acid variants or protein isoforms can be performed in conventional pathology labs. The invention provides kits for these tests. Kits of the present invention for detecting the presence or absence of a metastatic tumor can contain an antibody, a peptide or an aptamer that specifically binds to the ++ isoform (SEQ ID NO:2) or +++ isoform (SEQ ID NO:4) of Mena or Mena 11a (SEQ ID NO:24). Alternatively, or in addition, the kits can contain a probe or PCR primers that specifically hybridize to nucleic acid encoding the ++ isoform (SEQ ID NO:2) or +++ isoform (SEQ ID NO:4) of Mena or Mena 11a (SEQ ID NO:24). The nucleic acid encoding the ++ isoform of Mena can have the nucleotide sequence set forth in SEQ ID NO:1. The nucleic acid encoding the +++ isoform of Mena can have the nucleotide sequence set forth in SEQ ID NO:3. The nucleic acid encoding Mena 11a can have the nucleotide sequence set forth in SEQ ID NO:25. The kits can include agents for detecting two of, or all of, Mena++, Mena+++ and Mena 11a.

The present invention is illustrated in the following Experimental Details section, which is set forth to aid in the understanding of the invention, and should not be construed to limit in any way the scope of the invention as defined in the claims that follow thereafter.

EXPERIMENTAL DETAILS

Materials and Methods

Isolation of Invasive Tumor Cells by In Vivo Invasion Assay and Fluorescence-Activated Cell Sorting of Primary Tumor Cells.

MTLn3-derived mammary tumors in rats (Wang et al., 2004), the PyMT driven mouse breast cancer transgenic model, and the in vivo invasion assay were used as described previously (Wang et al., 2004; Wyckoff et al., 2000) to study the gene expression pattern of invasive subpopulations of carcinoma cells within live primary tumors. The in vivo invasion assay uses microneedles filled with Matrigel and growth factors to collect invasive tumor cells from primary tumors. Microneedles are held in a clamping device and positioned in the primary tumor with a micromanipulator. One tenth of the volume from each needle was used to determine the number of cells collected. Collected cells were a mixture of carcinoma cells (75%) and macrophages (25%). From the remaining 9/10 volume from the microneedle, macrophages were removed by magnetic separation using CD11b beads (Mitenyl Biotech, USA), and RNA was extracted from purified carcinoma cells as described before (Wang et al., 2004). To isolate the average primary tumor cells (APTCs), a small piece of tumor was separated from the whole tumor, minced, and filtered twice through a nylon filter to obtain a single cell suspension. To isolate the tumor cells from blood, right auricular puncture was performed in anesthetized animals; red blood cells were lysed using ammonium chloride lysis buffer. To purify cancer cells from the lung metastasis, a portion of the lung was minced, and filtered twice through a nylon filter to obtain a single cell suspension. Fluorescence-activated cell sorting (FACS) was performed on the resulting single cell suspensions based on their green fluorescent protein (GFP) expression in tumor cells. GFP-positive tumor cells were collected into a tube and lysed directly for RNA extraction. All of the procedures were done on ice or at 4° C.

Controls for Invasion Specific Gene Expression Pattern.

To detect microneedle-sampling effects on gene expression, cell lines used to prepare tumors and tumor cells FACs sorted from primary tumors were subjected to microneedle collection, matrigel, and epidermal growth factor (EGF). The gene patterns resulting from these stimuli were not related to the invasion signature shown previously (Wang et al., 2004) as the genes regulated by EGF and matrigel were removed from the final analysis. The effect of needle containment of the invasive cells after they enter the microneedle was analyzed and the data is presented in FIG. 6. Finally, concerning the effect of using antibody beads directed against invasive cells to separate cell types, the expression of genes related to the invasion signature of tumor cells is unaffected as shown in FIG. 7 and as discussed in the results and discussion section.

Thus, only the environment within the primary tumor generates the pattern of gene expression of invasive cells.

Cell Lines and Cell Culture.

MTLn3 rat adenocarcinoma, and human breast cancer cell lines MDA-231 and T47D were procured from the American Type Culture Collection (ATCC), Manassas, Va. The culture conditions for MTLn3 were alpha MEM with 5% FBS. MDA-231 and T47D were grown in Dulbecco/Vogt Modified Eagle's Minimal Essential Medium (DMEM) with 10% fetal bovine serum (FBS), insulin and Selenium.

RT-PCR and QRT-PCR.

Real time-polymerase chain reaction (RT-PCR) and quantitative real-time PCR (QRT-PCR) were performed using primers mentioned in Table 2. QRT-PCR was performed using SyBr Green kit, ABI 9700 sequence detector, and data analysis was performed using ABI Prism 2.0 software (Applied Biosystems Foster City, Calif.). A strategy for the primer sequence design is given in FIG. 5.

RACE, Cloning and Sequencing.

Figure 5:
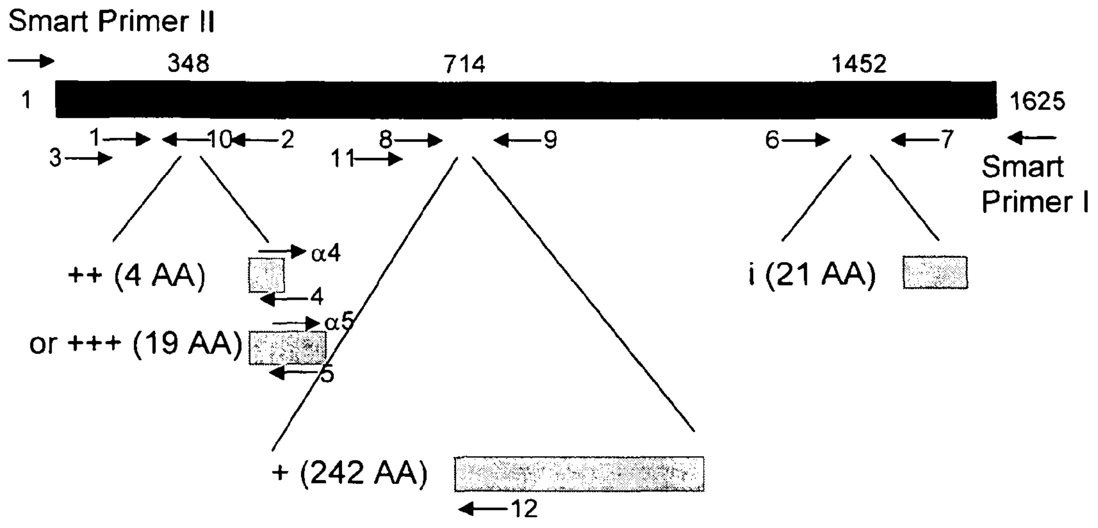
FIG. 5. Strategy for primer design for each of the Mena exons and Smart RACE.

Both 3' and 5 RACE were performed using Invitrogen RACE ready cDNA kit (sequences given in Table 2 and the RACE primer design strategy is given in FIG. 5) and cloned using Invitrogen TOPO TA cloning kit, following manufacturer's protocol. Briefly PCR was performed using two internal primers for the ++ and +++ sequences (Table 2) and an oligo dT primer for the 5' and poly G primer for the 3' ends. The PCR products were eluted form the gel and cloned into pCR-TOPO vector. The ligated vector was transformed into chemically competent cells; the selected clones were sequenced using M13 primers. Sequence alignment was performed using DNASTAR software.

TABLE 2

| Primer Sequences | | |
|---|---|---|
| **Mena primer sequences** | | |
| 1. | AGAGGATGCCAATGTCTTCG | (SEQ ID NO: 5) |
| 2. | TGTCTAGGCAATGTTGGCC | (SEQ ID NO: 6) |
| 3. | GATTCAAGACCATCAGGTTGTG (Forward primer for ++ and +++) | (SEQ ID NO: 7) |
| 4. | CAATGTTGGCCCTAAATAGAA (++ specific reverse primer) | (SEQ ID NO: 8) |
| d4. | TTCTATTTAGGGCCAACATTG (++ specific forward primer for RACE) | (SEQ ID NO: 9) |
| 5. | TACATCGCAAATTAGTGCTGTC (+++ specific reverse primer) | (SEQ ID NO: 10) |
| d5. | GACAGCACTAATTTGCGATGT (+++ specific forward primer for RACE) | (SEQ ID NO: 11) |
| 6. | CCAACCAGAAAACCTTGGG (external forward primer for 11a) | (SEQ ID NO: 12) |
| 7. | TGCTTCAGCCTCTCATAGTCA (external forward primer for 11a) | (SEQ ID NO: 13) |
| 8. | GAGCGAGAGAGGCAGAG | (SEQ ID NO: 14) |
| 9. | GCTCGGAAGCAGAGGAGTCT | (SEQ ID NO: 15) |
| 10. | TTCTCCTTGGAGAATCCCG (11a specific reverse primer) | (SEQ ID NO: 23) |
| **Pan Mena Primer** | | |
| Forward: | CGGCAGTAAGTCACCTGTCA | (SEQ ID NO: 16) |
| Reverse: | CTTCAGCTTTGCCAGCTCTT | (SEQ ID NO: 17) |

TABLE 2-continued

| Primer Sequences | | |
|---|---|---|
| Smart Primers | | |
| SMART II ™ A Oligonucleotide for RACE | | |
| AAGCAGTGGTATCAACGCAGAGTACGCGGG | | (SEQ ID NO: 18) |
| 3'-RACE CDS Primer A (SMART I) for RACE | | |
| AAGCAGTGGTATCAACGCAGAGTACT (T) 30V N (N = A, C, G, or T; V = A, G, or C) | | (SEQ ID NO: 19) |
| 5'-RACE CDS Primer A (T) 25V N (N = A, C, G, or T; V = A, G, or C) | | (SEQ ID NO: 20) |
| Long: | CTAATACGACTCACTATAGGGCAAGC AGTGGTATCAACGCAGAGT | (SEQ ID NO: 21) |
| Short: | CTAATACGACTCACTATAGGGC | (SEQ ID NO: 22) |

Results and Discussion

Specific isoforms of Mena that are upregulated or downregulated in invasive breast cancer cells have been identified. Different models were utilized including the MTLn3 rat adenocarcinoma allograft model, the PyMT mouse transgenic breast cancer model and a number of human breast cancer cell lines. Mena expression is upregulated 3-4 fold in invasive primary breast cancer cells (Wang et al., 2004). Controls done to determine the effects of manipulations used to collect invasive tumor cells from the primary mammary tumor demonstrate that the expression of the invasion isoform of Mena is not induced by cell collection. Only the tumour microenvironment induces the expression of these isoforms. In this study the stability of this overexpression was determined, i.e. the invasive cells collected by in vivo invasion assay showed a 3-4 fold upregulation in Mena expression when compared to APTCs. Therefore, the cells were followed and separated from the blood and from the lung met. Using the MTLn3 and mouse PyMT transgenic models, the invasive cells were collected and separated by in vivo invasion assay, and the APTCs by FACS sorting.

Figure 1B:
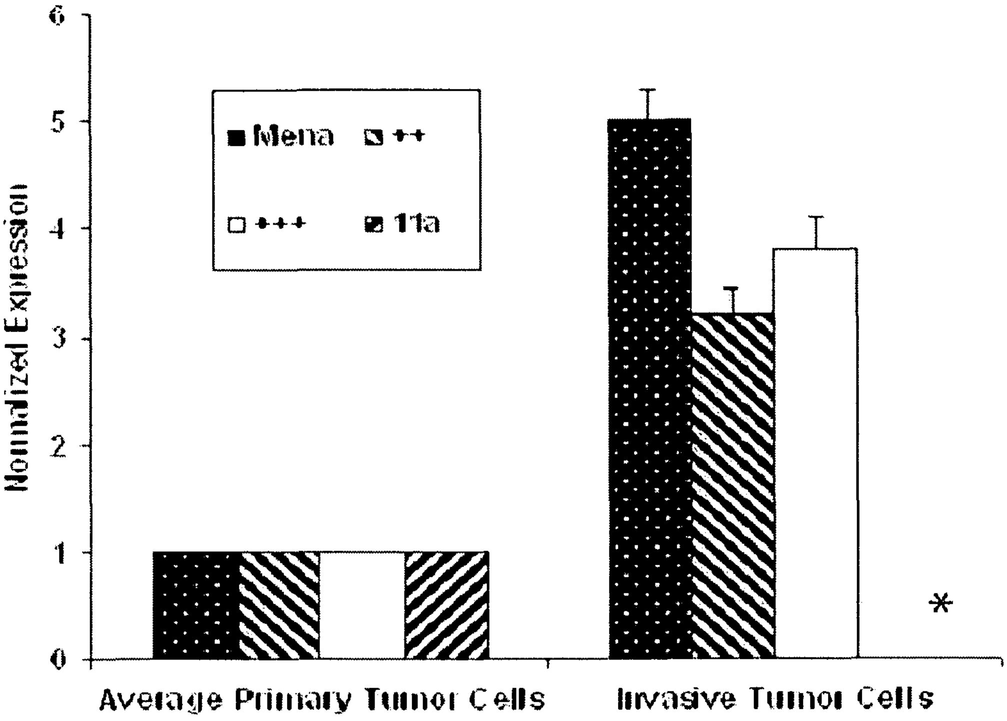

RT-PCR analysis showed that amplicons containing the Mena++ and Mena+++ exons were upregulated while amplicons containing Mena 11a were downregulated specifically in the invasive tumor cell population as compared to the APTC. QRT-PCR studies confirmed the RT-PCR finding and showed upregulation of both ++ and +++ exons and the downregulation of the 11a exon specifically in the invasive tumor cells isolated from both mammary tumor models, MTLn3 (FIG. 1A) and mouse PyMT model (FIG. 1B). An amplicon specific for the + exon was also detected in APTC and invasive tumor cells. Similar levels of a splice variant that did not contain either the ++ or the +++ was detected in both invasive tumor cells and APTC. This indicates that the increased expression of pan Mena are mainly due to the splice variants ++ and +++.

Figure 2:
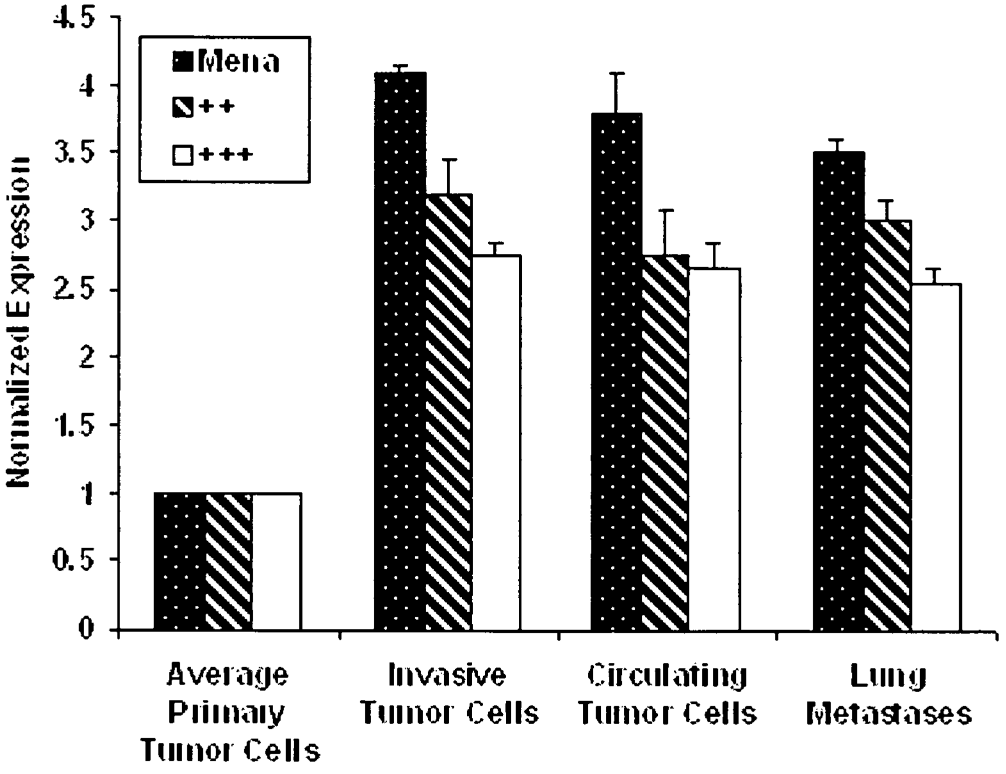
FIG. 2. Mena isoforms ++ and +++ are over-expressed in metastatic MTLn3 cells as determined by QRT-PCR. The pan Mena primer shows a four fold over-expression in the invasive cells. The ++ and +++ isoforms characteristic of invasive tumor cells show over expression in the invasive tumor cells, circulating tumor cells in blood and in tumor cells growing as lung mets. The error bars show standard errors of mean (SEM) performed on three biological repeats and three technical repeats.
Figure 3:
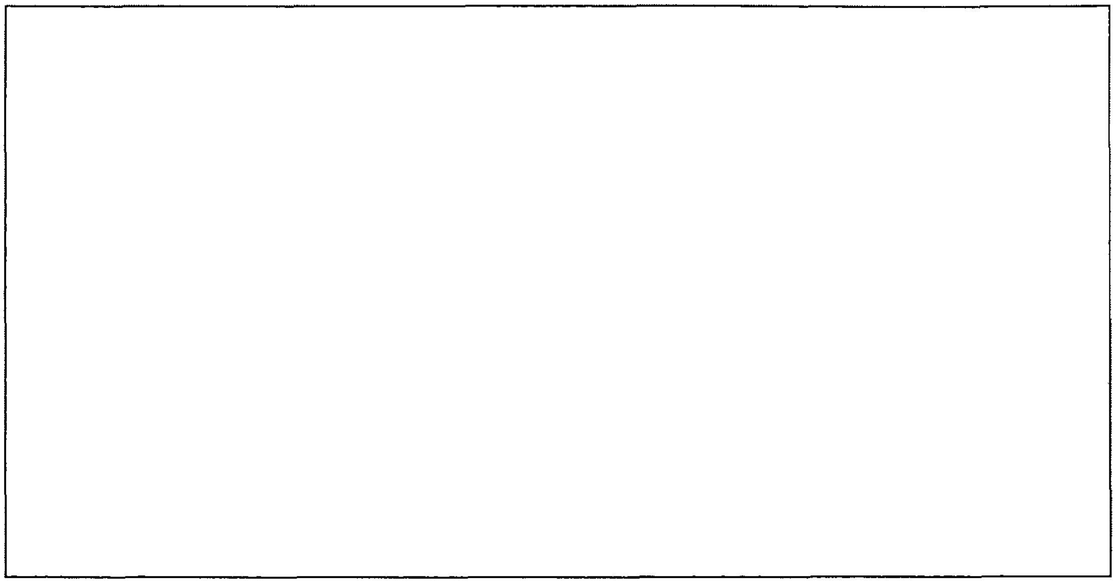
FIG. 3. Mena +++ splice variant is expressed in human breast cancer cell lines. MDA231 shown on left and T47D shown on right.

FIG. 2 shows that the ++ and +++ splice variant of Mena message remains up-regulated in the cells that have intravasated into blood and the cells that have formed successful metastases (mets) in the lung. This indicates that the change in expression level is due to a stable genetic change in the metastatic cells. The 11a splice variant was not detected in the lung metastasis indicating at least an eight fold down regulation.

The results of the RT-PCR and QRT-PCR showed that both the ++ and +++ exons are up-regulated in the invasive cells. However, it was unclear if the exons are present in a single transcript or on separate transcripts. To address this question, ++ and +++ bearing transcripts from the invasive PyMT mouse transgenic tumors were cloned and sequenced. RACE analysis was selected in order to identify transcripts that contained the ++ and +++ exons. The results provide a consensus sequence from at least 10 clones for each transcript. The results show a 100% match with the published mouse sequences and demonstrated that the ++ and +++ exons are in separate transcripts. The alignments for the ++ and +++ sequences are shown in FIG. 4.

Figure 6:
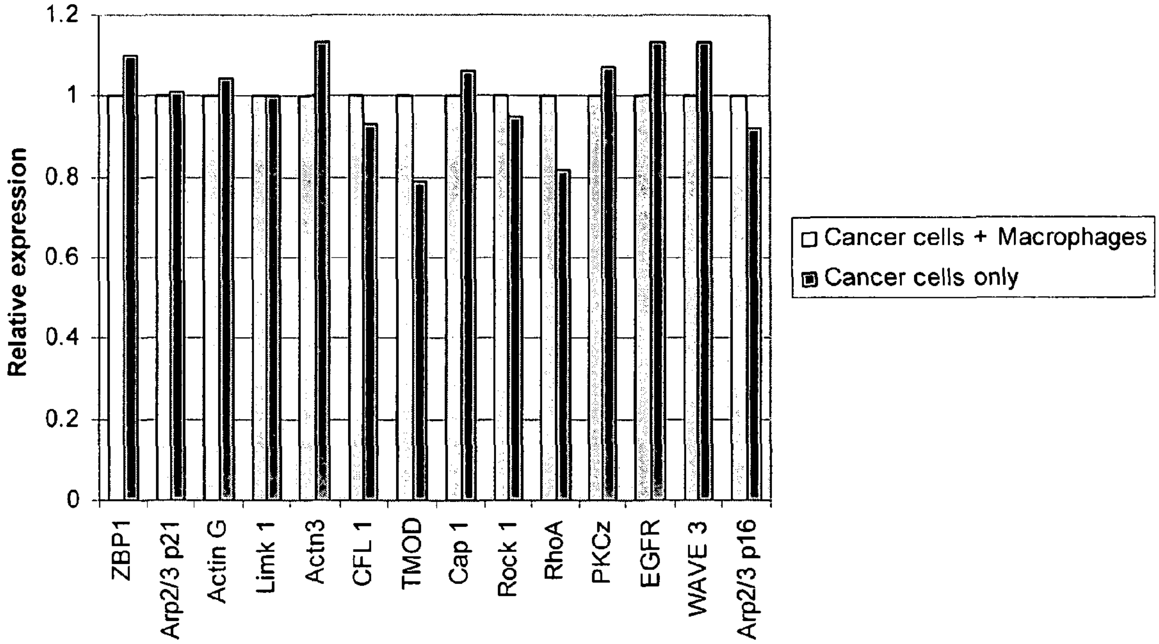
FIG. 6. Effect of magnetic bead separation process in the gene expression pattern of the invasive cells.
Figure 7:
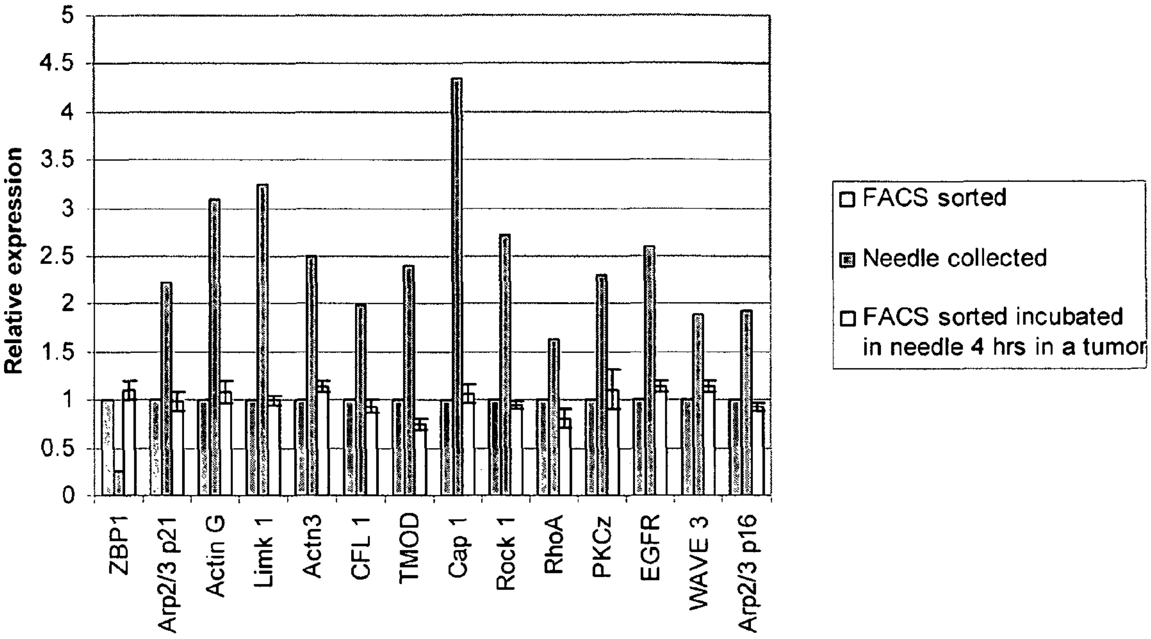
FIG. 7. Effect of needle containment in the gene expression pattern of the invasive cells.

FIGS. 6 and 7 show that both the 2+ and 3+ variants remain elevated at the mRNA level in tumor cells circulating in the blood, thus making possible a blood assay for these variants. PCR, nucleic acid probes and/or antibody staining can thus be used to diagnose metastatic disease using a blood sample.

Figure 8:
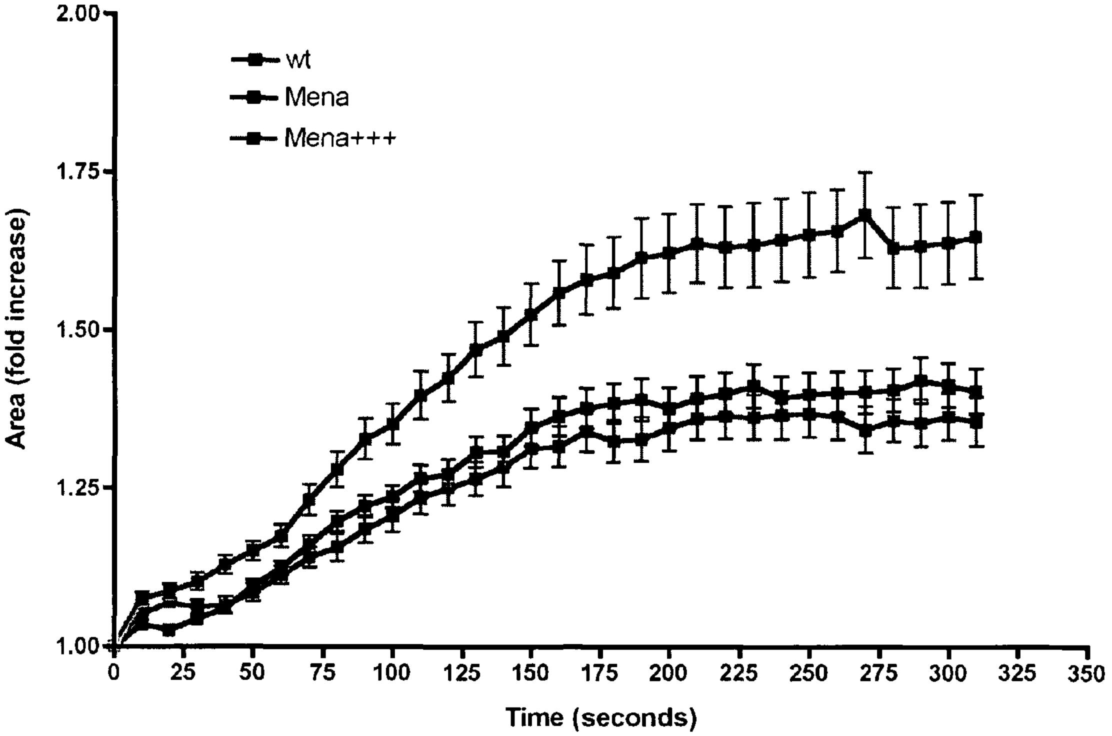
FIG. 8. Enhancement of tumor cell migration when Mena 3+ is expressed. Area is a measure of cell migration. wt=wild type.
Figure 9:
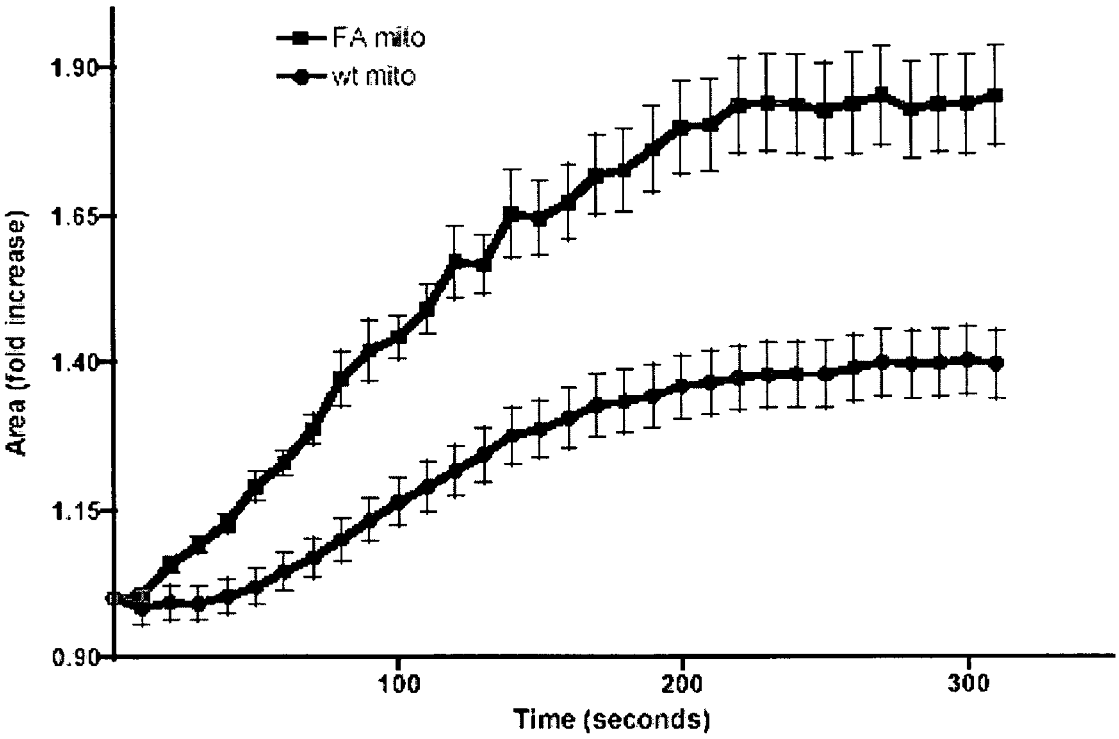
FIG. 9. Inhibition of metastatic tumor cell migration when Mena is inhibited with mito, a molecule that redirects Mena to the wrong place in the cell.

FIG. 8 shows enhancement of tumor cell migration when Mena 3+ is expressed. Importantly, as shown in FIG. 9, inhibition of metastatic tumor cell migration occurs when Mena is inhibited, in this case using mito, a molecule that redirects Mena to the wrong place in the cell. This result establishes that inhibition of Mena function inhibits migration of metastatic cells and therefore is a good strategy for inhibiting metastasis.

Figure 10:
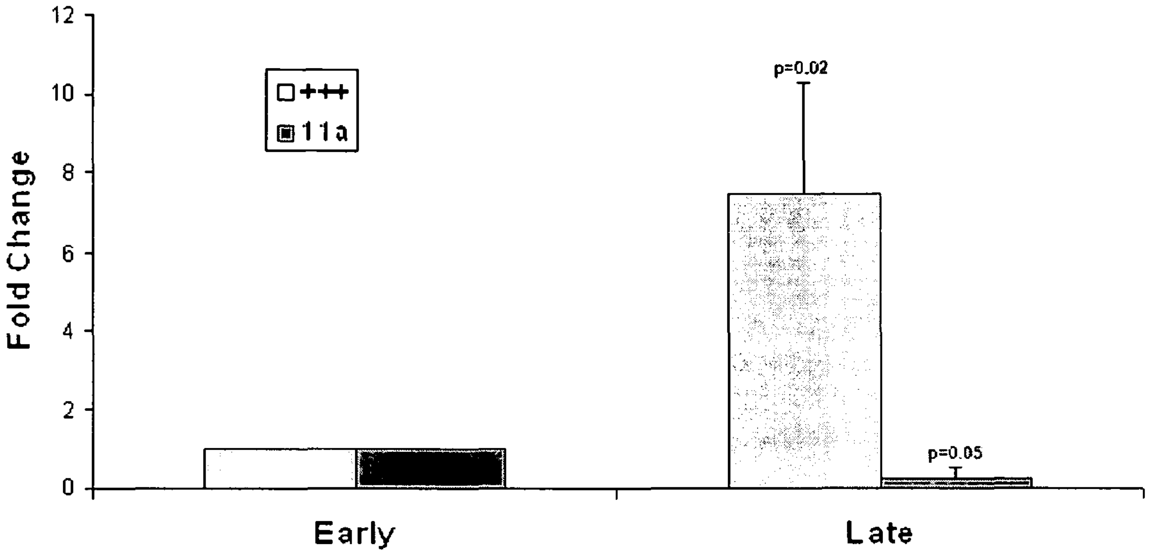
FIG. 10. QRT-PCR assessment of Mena splice variant expression in FNA samples from PyMT induced mouse mammary tumors. Levels of Mena+++ and Mean 11a in metastatic tumors (n=9) were compared to those found in adenomas/MIN (n=9). The result is expressed as fold change. Error bars show standard error of mean and p values indicate results of Student T test.

Fine Needle Aspiration (FNA) biopsies were performed on 18 mice with PyMT induced mammary tumors ranging in age from 10 to 26 weeks. Nine animals had 2-3 mm tumors at the stage of adenoma/MIN without any signs of invasion, and 9 mice had 1-2 cm invasive carcinomas with histologically confirmed lung metastasis. FNA obtained material was snap frozen in liquid nitrogen and stored at −163° C. prior to QRT-PCR analysis. Good quality RNA was isolated from all 18 samples with amount ranging from 0.5-2 μg. Tumors were grouped according to the stage into: 1) early tumors (adenomas/MIN) and 2) late tumors (invasive metastatic carcinomas). The difference in Mena isoform expression is shown as a fold change in invasive metastatic carcinomas compared to adenomas/MINs (FIG. 10). A 7.5 fold increase in Mena+++ expression was observed in metastatic carcinomas when compared with adenomas/MINs. Expression of Mena 11a decreased to 30% in invasive lesions.

Figure 11:
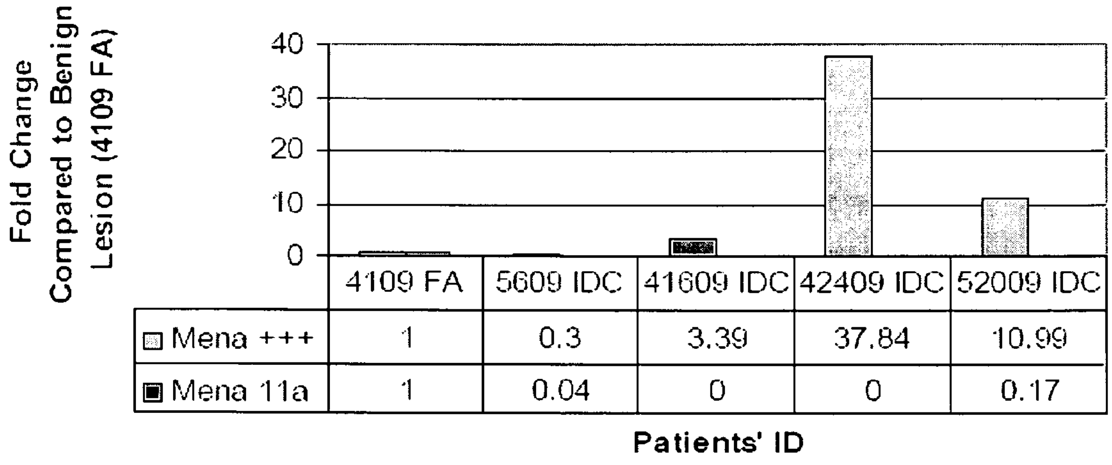
FIG. 11. QRT-PCR assessment of Mena splice variant expression in FNA samples from human breast lesions. Levels of Mena+++ and Mena 11a in 4 invasive ductal carcinomas (IDC) were compared to those found in a fibroadenoma (FA). The result is expressed as a fold change.

Tissue was also obtained by FNA biopsy for QRT-PCR analysis of Mena+++ and Mena 11a isoforms for 4 invasive ductal carcinomas (IDC) of the breast and one fibroadenoma (FA). IDC carcinomas were classified according to the Bloom Richardson scale as follows: 1 moderately and 3 poorly differentiated. The clinical and demographical data including patients' age tumor size, lymph node status, estrogen, progesterone and Her2Neu receptor status as well as RNA yield are listed in Table 3. FIG. 11 shows a fold change of Mena isoform expression in 4 invasive breast carcinomas compared to a fibroadenoma. Three IDC showed increased Mena+++ expression ranging from 3-37-fold. In IDC patient 5609, the Mena+++/11a ratio is elevated even though in this subject the expression of Mena+++ is decreased. The calculated ratio of expression of Mena +++/11a is 7.5 in patient 5609, which is significantly elevated compared to control at 1. Mena 11a was exceedingly low or not detectable in the 4 IDC patients.

Based on the above data, a molecular probe, either nucleic acid or antibody or both, against either the ++ or +++ variant and 11a variant would provide an important diagnostic/prognostic tool. Analysis of the relative levels of $Mena^{+++}$ and/or $Mena^{++}$ versus Mena 11a in tumor tissue can provide a ratiometric prognostic marker for metastasis. Since the up-regulation of expression of the ++ and +++ exons observed here is a stable change in invasive and metastatic mammary tumor cells, probes specifically directed at these exons would be powerful diagnostic markers for the presence of metastatic cells and therefore the potential of metastatic disease.

All human adenocarcinomas are derived from epithelial organs that may share a common morphogenetic strategy at the molecular level (Condeelis and Pollard, 2006; Wang et al., 2004, 2005). The invasion signature, of which Mena 2+ and 3+ are invasion isoforms, predicts that the same morphogenetic strategy is used for normal organ morphogenesis and tumor metastasis. This suggests that Mena 2+ and 3+ will be useful targets for the diagnosis and therapy of all common adenocarcinomas in adult humans. In particular, the invention described herein will be applicable to tumors such as breast, prostate, pancreas, colon, brain, liver, lung, and head and neck tumors.

TABLE 3

Clinical and demographical patient data

| Clinical and Pathological Parameters | PATIENT ID 4109 | 5609 | 41609 | 42409 | 52009 |
|---|---|---|---|---|---|
| Diagnosis | FA* | IDC** | IDC** | IDC** | IDC** |
| Grade | NA*** | 6/9 | 9/9 | 8/9 | 8/9 |
| Size | 4.0 × 3.3 × 1.5 | 2.5 × 2.0 × 1.7 | 1.5 × 1.4 × 1.1 | 5.1 × 1.6 × 1.2 | 1.7 × 1.6 × 1.2 |
| ER | NA | + | − | + | − |
| PR | NA | + | − | + | − |
| Her2 | NA | 1-2+ | − | − | 2+ |
| Lymph Node Metastasis | NA | 10/21 | 0/5 | Micrometastases (>2 mm) | NYE**** |
| Age | 20 | 59 | 71 | 72 | 75 |
| Mena+++ Fold Change | NA | 0.3 | 3.39 | 34.84 | 10.99 |
| RNA (μg) | 2.38 | 4.4 | 1.2 | 3.76 | 3.4 |

*Fibroadenoma;
**Invasive Ductal Carcinoma;
***Not Applicable;
****Not yet Examined

REFERENCES

Barzik M, Kotova T I, Higgs H N et al. Ena/VASP proteins enhance actin polymerization in the presence of barbed end capping proteins. J Biol Chem. 2005 Aug. 5; 280(31): 28653-62.

Brinkman B M. Splice variants as cancer biomarkers. Clin Biochem. 2004 July; 37(7):584-94.

Condeelis and Pollard (2006) Macrophages: Obligate partners for tumor cell migration, invasion, and metastasis. Cell 124: 263-266.

Condeelis J, Singer R H, Segall J E. The great escape: when cancer cells hijack the genes for cheniotaxis and motility. Annu Rev Cell Dev Biol. 2005; 21: 695-718.

Di Modugno F, Bronzi G, Scanlan M J et. al. Human Mena protein, a serex-defined antigen overexpressed in breast cancer eliciting both humoral and CD8+ T-cell immune response. Int J. Cancer. 2004 May 10; 109(6):909-18.

Gertler F B, Niebuhr K, Reinhard M et. al. Mena, a relative of VASP and Drosophila Enabled, is implicated in the control of microfilament dynamics. Cell. 1996 Oct. 18; 87(2):227-39.

Kamai T, Tsujii T, Arai K, Takagi K, Asami H, Ito Y, Oshima H. Significant association of Rho/ROCK pathway with invasion and metastasis of bladder cancer. Clin Cancer Res. 2003 July; 9(7):2632-41.

Kuhnel K, Jarchau T, Wolf E et. al. The VASP tetramerization domain is a right-handed coiled coil based on a 15-residue repeat. Proc Natl Acad Sci USA. 2004 Dec. 7; 101(49): 17027-32.

Loureiro J J, Rubinson D A, Bear J E et. al. Critical roles of phosphorylation and actin binding motifs, but not the central proline-rich region, for Ena/vasodilator-stimulated phosphoprotein (VASP) function during cell migration. Mol Biol Cell. 2002 July; 13 (7):2533-46.

Otsubo T, Iwaya K, Mukai Y, Mizokami Y, Serizawa H, Matsuoka T, Mukai K. Involvement of Arp2/3 complex in the process of colorectal carcinogenesis. Mod Pathol. 2004 April; 17(4):461-7.

Prehoda K E, Lee D J, Lim W A. Structure of the enabled/VASP homology 1 domain-peptide complex: a key component in the spatial control of actin assembly. Cell. 1999 May 14; 97(4):471-80.

Sambrook J and Russell D W. Molecular Cloning. A Laboratory Manual, third edition, Cold Spring Harbor Laboratory Press, 2001.

Scott J A, Shewan A M, den Elzen N R et. al. Ena/VASP proteins can regulate distinct modes of actin organization at cadherin-adhesive contacts. Mol Biol Cell. 2006 March; 17(3):1085-95.

Urbanelli L, Massini C, Emiliani C et. al. Characterization of human Enah gene. Biochim Biophys Acta. 2006 January-February; 1759(1-2):99-107.

Venables J P. Unbalanced alternative splicing and its significance in cancer. Bioessays. 2006 April; 28(4):378-86.

Wang W, Goswami S, Lapidus K, et. al. Identification and testing of a gene expression signature of invasive carcinoma cells within primary mammary tumors. Cancer Res. 2004 Dec. 1; 64(23):8585-94.

Wang, Goswami, Sahai, Wyckoff, Segall, Condeelis (2005) Tumor Cells caught in the act of invading: their strategy for enhanced cell motility. Trends Cell Biol. 15:138-145.

Wang W, Mouneimne G, Sidani M et. al The activity status of cofilin is directly related to invasion, intravasation, and metastasis of mammary tumors. J Cell Biol. 2006 May 8; 173(3):395-404.

Wyckoff J B, Segall J E, Condeelis J S. The collection of the motile population of cells from a living tumor. Cancer Res. 2000 Oct. 1; 60(19):5401-4.

What is claimed is:

1. A method for determining whether a subject has a metastatic tumor comprising assaying a blood, tissue and/or tumor sample of the subject for expression of the ++ and/or +++ and 11a variants of Mena, wherein expression of the ++ and/or +++ variant of Mena is compared to expression of Mena 11a and wherein overexpression of the ++ and/or +++ variant of Mena compared to expression of Mena 11a indicates the presence of a metastatic tumor.

2. The method of claim 1, wherein the tumor is a secretory epithelial tumor.

3. The method of claim 1, wherein the tumor is a breast, pancreas, prostate, colon, brain, liver, lung, head or neck tumor.

4. The method of claim 1, wherein the sample is assayed using an agent that specifically binds to the ++ isoform (SEQ ID NO:2) or +++ isoform (SEQ ID NO:4) of Mena or to nucleic acid encoding the ++ isoform or +++ isoform of Mena.

5. The method of claim 4, wherein the agent is an antibody, a peptide or an aptamer.

6. The method of claim 4, wherein the agent is labeled with a detectable marker.

7. The method of claim 1, wherein the sample is assayed for the ++ variant of Mena.

8. The method of claim 1, wherein the sample is assayed for the +++ variant of Mena.

9. The method of claim 1, wherein the sample is assayed for both the ++ variant and the +++ variant of Mena.

10. The method of claim 1, wherein overexpression of the ++ and/or +++ variant of Mena occurs in combination with overexpression of one or more of Arp 2/3 complex subunit p21, Arp 2/3 complex subunit p16, actinin alpha 3, capping protein alpha 1, epidermal growth factor receptor (EGFR), WAVE 3, actin gamma, LIM-kinase 1, cofilin 1, Rock 1, RhoA or protein kinase Cz.

11. The method of claim 1, wherein overexpression of the ++ and/or +++ variants and decreased expression of the 11a variant of Mena, together, indicate the presence of a metastatic tumor.

12. The method of claim 1, wherein the sample is assayed using an agent that specifically binds to Mena 11a (SEQ ID NO:24) or to nucleic acid encoding Mena 11a.

13. A method for assessing the efficacy of therapy to treat a metastatic tumor in a subject who has undergone or is undergoing treatment for a metastatic tumor, the method comprising assaying a blood, tissue and/or tumor sample of the subject for expression of the ++ and/or +++ and 11a variants of Mena, wherein expression of the ++ and/or +++ variant of Mena is compared to expression of Mena 11a and wherein overexpression of the ++ and/or +++ variant of Mena compared to expression of Mena 11a is indicative of a need to continue therapy to treat the tumor.

14. The method of claim 13, wherein overexpression of the ++ and/or +++ variants and decrease in expression of the 11a variant of Mena is indicative of a need to continue therapy to treat the tumor.

15. The method of claim 13, wherein the tumor is a secretory epithelial tumor.

16. The method of claim 13, wherein the tumor is a breast, pancreas, prostate, colon, brain, liver, lung, head or neck tumor.

17. The method of claim 13, wherein the sample is assayed for the ++ variant of Mena.

18. The method of claim 13, wherein the sample is assayed for the +++ variant of Mena.

19. The method of claim 13, wherein the sample is assayed for both the ++ variant and the +++ variant of Mena.

20. The method of claim 13, wherein the sample is assayed using an agent that specifically binds to the ++ isoform (SEQ ID NO:2) or +++ isoform (SEQ ID NO:4) of Mena or to nucleic acid encoding the ++ isoform or +++ isoform of Mena.

21. The method of claim 20, wherein the agent is an antibody, a peptide or an aptamer.

22. The method of claim 20, wherein the agent is labeled with a detectable marker.

23. The method of claim 13, wherein the sample is assayed using an agent that specifically binds to Mena 11a (SEQ ID NO:24) or to nucleic acid encoding Mena 11a.

24. A method for assessing the prognosis of a subject who has a metastatic tumor, comprising assaying a blood, tissue and/or tumor sample of the subject for expression of the ++ and/or +++ and 11a variants of Mena, wherein expression of the ++ and/or +++ variant of Mena is compared to expression of Mena 11a and wherein the subject's prognosis improves with a decrease in expression of the ++ and/or +++ variant of Mena compared to expression of Mena 11a.

25. The method of claim 24, wherein the subject's prognosis improves with a decrease in expression of the ++ and/or +++ variants of Mena and an increase in expression of the 11a variant of Mena.

26. The method of claim 24, wherein the tumor is a secretory epithelial tumor.

27. The method of claim 24, wherein the tumor is a breast, pancreas, prostate, colon, brain, liver, lung, head or neck tumor.

28. The method of claim 24, wherein the sample is assayed for the ++ variant of Mena.

29. The method of claim 24, wherein the sample is assayed for the +++ variant of Mena.

30. The method of claim 24, wherein the sample is assayed for both the ++ variant and the +++ variant of Mena.

31. The method of claim 24, wherein the sample is assayed using an agent that specifically binds to the ++ isoform (SEQ ID NO:2) or +++ isoform (SEQ ID NO:4) of Mena or to nucleic acid encoding the ++ isoform or +++ isoform of Mena.

32. The method of claim 31, wherein the agent is an antibody, a peptide or an aptamer.

33. The method of claim 31, wherein the agent is labeled with a detectable marker.

34. The method of claim 24, wherein the sample is assayed using an agent that specifically binds to Mena 11a (SEQ ID NO:24) or to nucleic acid encoding Mena 11a.

* * * * *

SEQUENCE LISTING

<160> NUMBER OF SEQ ID NOS: 25

<210> SEQ ID NO 1
<211> LENGTH: 12
<212> TYPE: DNA
<213> ORGANISM: Human

<400> SEQUENCE: 1
ttctatttag gg 12

<210> SEQ ID NO 2
<211> LENGTH: 4
<212> TYPE: PRT
<213> ORGANISM: Human

<400> SEQUENCE: 2

Phe Tyr Leu Gly
1

<210> SEQ ID NO 3
<211> LENGTH: 57
<212> TYPE: DNA
<213> ORGANISM: Human

<400> SEQUENCE: 3
gcccagagca aggttactgc tacccaggac agcactaatt tgcgatgtat tttctgt 57

<210> SEQ ID NO 4
<211> LENGTH: 19
<212> TYPE: PRT
<213> ORGANISM: Human

<400> SEQUENCE: 4

Ala Gln Ser Lys Val Thr Ala Thr Gln Asp Ser Thr Asn Leu Arg Cys
1 5 10 15

Ile Phe Cys

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
agaggatgcc aatgtcttcg 20

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
tgtctaggca atgttggcc 19

<210> SEQ ID NO 7
<211> LENGTH: 22
<212> TYPE: DNA
<213> ORGANISM: Artificial Sequence
<220> FEATURE:
<223> OTHER INFORMATION: Forward primer for Mena ++ and +++

-continued

<400> SEQUENCE: 7
gattcaagac catcaggttg tg 22

<210> SEQ ID NO 8
<211> LENGTH: 21
<212> TYPE: DNA
<213> ORGANISM: Artificial Sequence
<220> FEATURE:
<223> OTHER INFORMATION: Mena ++ specific reverse primer

<400> SEQUENCE: 8
caatgttggc cctaaataga a 21

<210> SEQ ID NO 9
<211> LENGTH: 21
<212> TYPE: DNA
<213> ORGANISM: Artificial Sequence
<220> FEATURE:
<223> OTHER INFORMATION: Mena ++ specific forward primer for RACE

<400> SEQUENCE: 9
ttctatttag ggccaacatt g 21

<210> SEQ ID NO 10
<211> LENGTH: 22
<212> TYPE: DNA
<213> ORGANISM: Artificial Sequence
<220> FEATURE:
<223> OTHER INFORMATION: Mena +++ specific reverse primer

<400> SEQUENCE: 10
tacatcgcaa attagtgctg tc 22

<210> SEQ ID NO 11
<211> LENGTH: 21
<212> TYPE: DNA
<213> ORGANISM: Artificial Sequence
<220> FEATURE:
<223> OTHER INFORMATION: Mena +++ specific forward primer for RACE

<400> SEQUENCE: 11
gacagcacta atttgcgatg t 21

<210> SEQ ID NO 12
<211> LENGTH: 19
<212> TYPE: DNA
<213> ORGANISM: Artificial Sequence
<220> FEATURE:
<223> OTHER INFORMATION: External forward primer for Mena 11a

<400> SEQUENCE: 12
ccaaccagaa aaccttggg 19

<210> SEQ ID NO 13
<211> LENGTH: 21
<212> TYPE: DNA
<213> ORGANISM: Artificial Sequence
<220> FEATURE:
<223> OTHER INFORMATION: External reverse primer for Mena 11a

<400> SEQUENCE: 13
tgcttcagcc tctcatagtc a 21

<210> SEQ ID NO 14
<211> LENGTH: 17
<212> TYPE: DNA

-continued

<213> ORGANISM: Artificial Sequence
<220> FEATURE:
<223> OTHER INFORMATION: Primer

<400> SEQUENCE: 14
gagcgagaga ggcagag 17

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gctcggaagc agaggagtct 20

<210> SEQ ID NO 16
<211> LENGTH: 20
<212> TYPE: DNA
<213> ORGANISM: Artificial Sequence
<220> FEATURE:
<223> OTHER INFORMATION: Pan Mena forward primer

<400> SEQUENCE: 16
cggcagtaag tcacctgtca 20

<210> SEQ ID NO 17
<211> LENGTH: 20
<212> TYPE: DNA
<213> ORGANISM: Artificial Sequence
<220> FEATURE:
<223> OTHER INFORMATION: Pan Mena reverse primer

<400> SEQUENCE: 17
cttcagcttt gccagctctt 20

<210> SEQ ID NO 18
<211> LENGTH: 30
<212> TYPE: DNA
<213> ORGANISM: Artificial Sequence
<220> FEATURE:
<223> OTHER INFORMATION: SMART Primer II for RACE

<400> SEQUENCE: 18
aagcagtggt atcaacgcag agtacgcggg 30

<210> SEQ ID NO 19
<211> LENGTH: 57
<212> TYPE: DNA
<213> ORGANISM: Artificial Sequence
<220> FEATURE:
<223> OTHER INFORMATION: SMART Primer I for RACE
<220> FEATURE:
<221> NAME/KEY: misc_feature
<222> LOCATION: (57)..(57)
<223> OTHER INFORMATION: n is a, c, t or g

<400> SEQUENCE: 19
aagcagtggt atcaacgcag agtactvvvv vvvvvvvvvv vvvvvvvvvv vvvvvvn 57

<210> SEQ ID NO 20
<211> LENGTH: 28
<212> TYPE: DNA
<213> ORGANISM: Artificial Sequence
<220> FEATURE:
<223> OTHER INFORMATION: 5'-RACE CDS Primer
<220> FEATURE:

-continued

```
<221> NAME/KEY: misc_feature
<222> LOCATION: (28)..(28)
<223> OTHER INFORMATION: n is a, c, g or t

<400> SEQUENCE: 20

atvvvvvvvv vvvvvvvvvv vvvvvvvn                                          28


<210> SEQ ID NO 21
<211> LENGTH: 45
<212> TYPE: DNA
<213> ORGANISM: Artificial Sequence
<220> FEATURE:
<223> OTHER INFORMATION: Primer

<400> SEQUENCE: 21

ctaatacgac tcactatagg gcaagcagtg gtatcaacgc agagt                       45


<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22

ctaatacgac tcactatagg gc                                                22


<210> SEQ ID NO 23
<211> LENGTH: 19
<212> TYPE: DNA
<213> ORGANISM: Artificial Sequence
<220> FEATURE:
<223> OTHER INFORMATION: 11a specific reverse primer

<400> SEQUENCE: 23

ttctccttgg agaatcccg                                                    19


<210> SEQ ID NO 24
<211> LENGTH: 21
<212> TYPE: PRT
<213> ORGANISM: human

<400> SEQUENCE: 24

Arg Asp Ser Pro Arg Lys Asn Gln Ile Val Phe Asp Asn Arg Ser Tyr
1               5                   10                  15

Asp Ser Leu His Arg
            20


<210> SEQ ID NO 25
<211> LENGTH: 63
<212> TYPE: DNA
<213> ORGANISM: human

<400> SEQUENCE: 25

acgggattct ccaaggaaaa atcagattgt ttttgacaac aggtcctatg attcattaca      60

cag                                                                     63
```